US005753522A

United States Patent [19]
Polans et al.

[11] Patent Number: 5,753,522
[45] Date of Patent: May 19, 1998

[54] PURIFIED PROTEIN FOR IDENTIFYING A CANCER-ASSOCIATED RETINOPATHY AUTOANTIBODY

[75] Inventors: Arthur S. Polans, Portland, Oreg.; Krzysztof Palczewski, Seattle, Wash.

[73] Assignee: Legacy Good Samaritan Hospital and Medical Center, Portland, Oreg.

[21] Appl. No.: 419,102

[22] Filed: Apr. 10, 1995

Related U.S. Application Data

[63] Continuation-in-part of Ser. No. 804,894, Dec. 6, 1991, Pat. No. 5,405,749.

[51] Int. Cl.$^6$ .................... G01N 33/574; G01N 33/53
[52] U.S. Cl. .................... 436/518; 435/7.23; 436/64; 530/350
[58] Field of Search .................... 530/350; 435/7.23; 436/64, 518

[56] References Cited

U.S. PATENT DOCUMENTS 5,405,749  4/1995  Polans et al. .................... 435/7.23

OTHER PUBLICATIONS

Dizhoor, A.M., et al., Science, vol. 251, pp. 915–918, 22 Feb. 1991.
D. Denny–Brown, "Primary sensory neuropathy with muscular changes associated with carcinoma," *J. Neurol. Neurosurg. Psychiatr.*, 11:73–87, 1948.
W.R. Brain et al., "Subacute cortical cerebellar degeneration and its relation to carcinoma," *J. Neurol. Neurosurg. Psychiatr.*, 14:59–75, 1951.
A.M. Crestfield et al., "The preparation and enzymatic hydrolysis of reduced and S–carboxymethylated proteins," *J. Biol. Chem.*, 238:622–627, 1963.
P.B. Croft et al., "Carcinomatous neuromyopathy: its incidence in patients with carcinoma of the lung and carcinoma of the breast," *Lancet*, i:184–188, 1963.
L. Brain et al., The remote effects of cancer on the nervous system, Grune & Stratton, New York, 1965.
L. Brain et al., "Subacute cerebellar degeneration associated with neoplasms," *Brain*, 88:465–478, 1965.
C.Y. Lai, "Studies on the structure of rabbit muscle aldolase. I. Cleavage with cyanogen bromide: an approach to the determination of the total primary structure," *Arch. Biochem. Biophys.*, 128:202–211, 1968.
F. Norris, "The remote effects of cancer on the nervous system," *Z. Neurol.*, 201:201–210, 1972.
M. Bradford, "A rapid and sensitive method for the quantitation of microgram quantities of protein utilizing the principle of protein–dye binding," *Anal. Biochem.*, 72:248–254, 1976.
R.A. Sawyer et al., "Blindness caused by photoreceptor degeneration as a remote effect of cancer," *Am. J. Ophythalmol.*, 81:606–613, 1976.

A.S. Polans et al., "Light–induced dephosphorylation of two proteins in frog rod outer segments. Influence of cyclic nucleotides and calcium," *J. Gen. Physiol.*, 74:595–613, 1979.
S.C. Schold et al., "Subacute motor neuronopathy: A remote effect of lymphoma," *Ann. Neurol.*, 5:271–287, 1979.
R.J. Hawley et al., "The carcinomatous neuromyopathy of oat cell lung cancer," *Ann. Neurol.*, 7:65–72, 1980.
R.A. Henson et al., "Cancer and the nervous system: the Neurological manifestations of systemic malignant disease," *Blackwell Scientific, Oxford*, 346–367, 1982.
S.E. Kornguth et al., "Occurrence of anti–retinal ganglion cell antibodies in patients with small cell carcinoma of the lung," *Cancer*, 50:1289–1293, 1982.
Paul A. Bunn et al., "Paraneoplastic syndromes. In cancer: Principle and practice of oncology," *J.B. Lippincott & Co., Philedelphia*, 1797–1842, 1982.
D.S. Papermaster, "Preparation of retinal rod outer segments," *Methods Enzymol.*, 81:48–52, 1982.
U. Wildon et al., "Light–dependent phosphorylation of rhodopsin: number of phosphorylation sites," *Biochemistry*, 21:3014–3022, 1982.
J.L. Keltner et al., "Photoreceptor degeneration: possible autoimmune disorder," *Arch. Ophthalmol.* 101:564–569, 1983.
T.A.S. Buchanan et al., "An ultrastructural study of retinal photoreceptor degeneration associated with bronchial carcinoma," *Am. J. Ophthalmol.*, 97:277–287, 1984.
G.B. Grunwald et al., "Autoimmune basis for visual paraneoplastic syndrome in patients with small–cell lung carcinoma," *Lancet*, i:658–661, 1985.
J. Newsom–Davis, "Lambert–Eaton myasthenic syndrome," *Sem. Immunopathol.*, 8:129–140, 1985.
J.W. Crabb et al., "Complete primary structure of prostatropin, a prostate epithelial cell growth factor," *Biochemistry*, 25:4988–4993, 1986.
G.M.P. Galbraith et al., "Antibodies to neurofilament protein in retinitis pigmentosa," *J. Clin. Invest.*, 78:865–869, 1986.
J.E. Greenlee et al., "Anti–cerebellar antibodies in serum and cerebrospinal fluid of a patient with oat cell carcinoma of the lung and paraneoplastic cerebellar degeneration," *Ann. Neurol.*, 19:82–85, 1986.
P. Matsudaira, "Sequence from picomole quantities of proteins electroblotted onto polyvinylidene difluoride membranes," *J. Biol. Chem.*, 262:10035–10038, 1987.

(List continued on next page.)

*Primary Examiner*—Toni R. Scheiner
*Attorney, Agent, or Firm*—Stoel Rives LLP

[57] ABSTRACT

A composition useful in a method for diagnosing cancer-associated retinopathy including the steps of acquiring a purified aliquot of 26 kDa protein, and, utilizing the protein, or a unique fragment thereof, to perform a patient-serum assay to identify in a sample of a patient's serum the presence of autoantibodies to the 26 kDa protein autoantigen.

9 Claims, 3 Drawing Sheets

OTHER PUBLICATIONS

H. Schagger et al., "Tricine–sodium dodecyl sulfate–polyacrylamide gel electrophoresis for the separation of proteins in the range of 1–100kDa," *Anal. Biochem.*, 166:368–379, 1987.

C.E. Thirkill et al., "Cancer–associated retinopathy," *Arch Ophthalmol*, 105:372–375, 1987.

N.E. Anderson et al., "Paraneoplastic cerebellar degeneration: clinical–immunologic correlations," *Ann. Neurol.*, 24:559–567, 1988.

J.W. Crabb et al., "The complete primary structure of the cellular retinaldehyde–binding protein from bovine retina," *J. Biol. Chem.*, 263:18678–18687, 1988.

H.J. DeAizpurua et al., "Antagonism of voltage–gated calcium channels in small cell carcinomas of patients with and without Lambert–Eaton myasthenic syndromes by autoantibodies, w–conotoxin and adenosine," *Cancer Res.*, 48:4719–4724, 1988.

Y.I. Kim et al., "IgG from patients with Lambert–Eaton syndrome blocks voltage–dependent calcium channels," *Science (Wash. D.C.)*, 239:405–408, 1988.

A.S. Polans et al., "Sialoglycoproteins of the frog rod outer segmnet plasma membrane," *Invest. Ophythalmol Vis. Sci.* 29:1523–1532, 1988.

M.D. Burton et al., "The use of gold reagents to quantitate antibodies eluted from nitrocellulose blots: application to EM immunocytochemistry," *Anal. Biochem.*, 183:225–230, 1989.

D. Gurne et al., "Antiretinal antibody in serum of patients with age–related macular degeneration," *Invest. Ophthalmol. Vis. Sci.*, 30:366a, 1989.

C.E. Thirkill et al., "Cancer–associated retinopathy (CAR syndrome) with antibodies reacting with retina, optic–nerve and cancer cells," *N. Engl. J. Med.*, 321:1589–1594, 1989.

M.O.M. Tso, "Experiments on visual cells by nature and man: in search of treatment for photorecptor degeneration," *Invest. Ophthalmol. vis. Sci.*, 30:2430–2460, 1989.

H.F. Furneaux et al., "Autoantibody synthesis in the central nervous system of patients with paraneoplastic syndromes," *Neurology*, 40:1085–1091, 1990.

J. Huang et al., "Application of sodium dodecyl sulfate–gel electrophoresis to low molecular weight polypeptides," *Anal. Biochem.*, 188:114–117, 1990.

K.A. West et al., "Current Research in Protein Chemistry," *J.J. Villagranca, editor*, 37–48, 1990.

Arthur S. Polans et al., "A photoreceptor calcium binding protein is recognized by autoantibodies obtained from patients with cancer–associated retinopathy," *J. Cell Biol.*, 112:981–989, 1991.

Number of residues : 202.

|  | 1 | 2 | 3 | 4 |
|---|---|---|---|---|
| A. | .341 | .652 | 1.165 | 1.324 |
| B. | .045 | .053 | .043 | .062 |
| C. | .048 | .052 | .053 | .053 |

PURIFIED PROTEIN FOR IDENTIFYING A CANCER-ASSOCIATED RETINOPATHY AUTOANTIBODY

CROSS-REFERENCE TO RELATED APPLICATION

This is a continuation-in-part of application Ser. No. 07/804,894, filed Dec. 6, 1991, now U.S. Pat. No. 5,405,749.

BACKGROUND PUBLICATIONS

The following publications are referred to by corresponding number in this application, and their contents are hereby incorporated by reference into this disclosure as background information:

1. Brain, L., and F. H. Norris: The Remote Effects of Cancer on the Nervous System. Grune & Stratton, New York. 24, 1965.
2. Brain, L., and M. Wilkinson: Subacute cerebellar degeneration associated with neoplasms. Brain. 88:465–478, 1965.
3. Brain, W. R., P. M. Daniel, and J. G. Greenfield: Subacute cortical cerebellar degeneration and its relation to carcinoma. J. Neurol. Neurosurg. Psychiatr. 14:59–75, 1951.
4. Croft, P. B., and M. Wilkinson: Carcinomatous neuromyopathy: its incidence in patients with carcinoma of the lung and carcinoma of the breast. Lancet. i:184–188, 1963.
5. Denny-Brown, D.: Primary sensory neuropathy with muscular changes ssociated with carcinoma. J. Neurol. Neurosurg. Psychiatr. 11:73–87, 1948.
6. Hawley, R. J., M. H. Cohen, N. Saini, and V. W. Armbrustmacher: The arcinomatous neuromyopathy of oat cell lung cancer. Ann. Neurol. 7:65–72, 1980.
7. Henson, R. A., and H. Urich: Cancer and the Nervous System: The Neurological Manifestations of Systemic Malignant Disease. Blackwell Scientific, Oxford. 346–367, 1982.
8. Minna, J. D., and P. A. Bunn: Paraneoplastic syndromes. In Cancer: Principles and Practice of Oncology. V. T. Devita, S. A. Rosenberg, and S. Hellman, editors. J. B. Lippincott & Co., Philadelphia. 1476–1517, 1982.
9. Norris, F.: The remote effects of cancer on the nervous system. Z. Neurol. 201:201–210, 1972.
10. Sawyer, R. A., J. B. Selhorst, L. E. Zimmerman, and W. F. Hoyt: Blindness caused by photoreceptor degeneration as a remote effect of cancer. Am. J. Ophthalmol. 81:606–613, 1976.
11. Schold, S. C., E. S. Cho, and M. Somasundaram: Subacute motor neuronapathy: A remote effect of lymphoma. Ann. Neurol. 5:271–287, 1979.
12. Anderson, N. E., M. K. Rosenblum, and J. B. Posner: Paraneoplastic cerebellar degeneration: clinical-immunologic correlations. Ann. Neurol. 24:559–567, 1988.
13. Keltner, J. L., A. M. Roth, and R. S. Chang: Photoreceptor degeneration: possible autoimmune disorder. Arch. Ophthalmol. 101:564–569, 1983.
14. Kornguth, S. E., R. Klein, R. Appen, and J. Choate: Occurrence of antiretinal ganglion cell antibodies in patients with small cell carcinoma of the lung. Cancer. 50:1289–1293, 1982.
15. DeAizpurua, H. J., E. H. Lambert, G. E. Greismann, B. M. Olivera, and V. A. Lennon: Antagonism of voltage-gated calcium channels in small cell carcinomas of patients with and without Lambert-Eaton myasthenic syndromes by autoantibodies, w-conotoxin and adenosine. Cancer Res. 48:4719–4724, 1988.
16. Kim, Y. I., and E. Neher: IgG from patients with Lambert-Eaton syndrome blocks voltage-dependent calcium channels. Science (Wash. D.C.). 239:405–408, 1988.
17. Newsom-Davis, J.: Lambert-Eaton myasthenic syndrome. Sem. Immunopathol. 8:129–140, 1985.
18. Furneaux, H. F., L. Reich, and J. B. Posner: Autoantibody synthesis in the central nervous system of patients with paraneoplastic syndromes. Neurology. 40:1085–1091, 1990.
19. Greenlee, J. E., and H. I. Lipton: Anti-cerebellar antibodies in serum and cerebrospinal fluid of a patient with oat cell carcinoma of the lung and paraneoplastic cerebellar degeneration. Ann. Neurol. 19:82–85, 1986.
20. Buchanan, T. A. S., T. A. Gardiner, and D. B. Archer: An ultrastructural study of retinal photoreceptor degeneration associated with bronchial carcinoma. Am. J. Ophthalmol. 97:277–287, 1984.
21. Grunwald, G. B., M. A. Simmonds, R. Klein, and J. E. Kornguth: Autoimmune basis for visual paraneoplastic syndrome in patients with small cell lung carcinoma. Lancet. i:658–661, 1985.
22. Thirkill, C. E., P. Fitzgerald, R. C. Sergott, A. M. Roth, N. K. Tyler, and J. L. Keltner: Cancer-associated retinopathy (CAR syndrome) with antibodies reacting with retino, optic-nerve and cancer cells. N. Engl. J. Med. 321:1589–1594, 1989.
23. Thirkill, C. E., A. M. Roth, and J. L. Keltner: Cancer-associated retinopathy. Arch. Ophthalmol. 105:372–375, 1987.
24. Tso, M. O. M.: Experiments on visual cells by nature and man: in search of treatment for photoreceptor degeneration. Invest. Ophthalmol. Vis. Sci. 30:2430–2460, 1989.
25. Galbraith, G. M. P., D. Emerson, H. H. Fudenberg, C. J. Gibbs, and D. C. Gajdusek: Antibodies to neurofilament protein in retinitis pigmentosa. J. Clin. Invest. 78:865–869, 1986.
26. Gurne, D., D. P. Edward, N. Mangini, and M. O. M. Tso: Antiretinal antibodies in serum of patients with age-related macular degeneration. Invest. Ophthalmol. Vis. Sci. 30:366a, 1989.
27. Papermaster, D. S.: Preparation of retinal rod outer segments. Methods Enzymol. 81:48–52, 1982.
28. Polans, A. S., J. Hermolin, and M. D. Bownds: Light-induced dephosphorylation of two proteins in frog rod outer segments. Influence of cyclic nucleotides and calcium. J. Gen. Physiol. 74:595–613, 1979.
29. Polans, A. S., and M. D. Burton: Sialoglycoproteins of the frog rod outer segment plasma membrane. Invest. Ophthalmol. Vis. Sci. 29:1523–1532, 1988.
30. Huang, J., and H. Matthews: Application of sodium dodecylsulfate-gel electrophoresis to low molecular weight polypeptides. Anal. Biochem. 188:114–117, 1990.
31. Schagger, H., and G. von Jagow: Tricine-sodium dodecylsulfatepolyacrylamide gel electrophoresis for the separation of proteins in the range of 1–100 kDa. Anal. Biochem. 166:368–379, 1987.
32. Bradford, M.: A rapid and sensitive method for quantitation of microgram quantities of protein utilizing the principle of dye-binding. Anal. Bio-chem. 72:248–254, 1976.
33. Burton, M. D., L. T. Onstott, and A. S. Polans: The use of gold reagents to quantitate antibodies eluted from nitrocellulose blots: application to EM immunocytochemistry. Anal. Biochem. 183:225–230, 1989.
34. Wilden, U., and H. Kuthn: Light-dependent phosphorylation of rhodopsin number of phosphorylation sites. Biochemistry. 21:3014–3022, 1982.
35. Crestfield, A. M., S. Moore, and W. J. Stein: The preparation and enzymatic hydrolysis of reduced and S-carboxymethylated proteins. J. Biol. Chem. 238:622–627, 1963.
36. Lai, C. H.: Studies on the structure of rabbit muscle aldolase. I. Cleavage with cyanogen bromide: an approach on the determination of the total primary structure. Arch. Biochem. Biophys. 128:202–211, 1968.
37. Matsudaira, P.: Sequence from picomole quantities of proteins electroblotted onto polyvinylidene difluoride membranes. J. Biol. Chem. 262:10035–10038, 1987.
38. Crabb, J. W., L. G. Armes, S. A. Carr, C. M. Johnson, G. D. Roberts, R. S. Bordoli, and W. L. McKeehan: Complete primary structure of prostatropin, a prostate epithelial cell growth factor. Biochemistry. 25:4988–4993, 1986.
39. West, K. A., and J. W. Crabb: Current Research in Protein Chemistry. J. J. Villafranca, editor. 37–48, 1990.
40. Crabb, J. W., C. M. Johnson, S. A. Carr, L. G. Armes, and J. C. Saari: The complete primary structure of the cellular retinaldehyde-binding protein from bovine retina. J. Biol. Chem. 263:18678–18687, 1988.
41. Polans, Arthur S., Janina Bitzylko, John Crabb, and Krzysztof Palczewski: A photoreceptor calcium binding protein is recognized by autoantibodies obtained from patients with cancer-associated retinopathy. J. Cell Biol. 112:981–989, 1991.
42. Polans, Arthur S., Janina Buczylko, John Crabb, and Krzysztof Palczewski: Calcium-binding proteins in the retina. P. Hargrave, editor. Methods in Neurosciences, Volume 15:248–260, 1993.
43. Polans, Arthur S., M. D. Burton, T. L. Haley, John W. Crabb, and Krzysztof Palczewski: Recoverin, but not Visinin, is an autoantigen in the human retina identified with a cancer-associated retinopathy. Investigative Ophthalmology and Visual Sciences, 34:81–90, 1993.

BACKGROUND OF THE INVENTION

The present invention relates to diagnosis of cancer-associated retinopathy, and additionally, and in this context, to a method for identifying and purifying a cancer-associated retinopathy autoantigen, and performing patient-serum assays using the purified autoantigen to identify in a patient's serum the presence of autoantibodies to the autoantigen.

Various neurodegenerative diseases are known to be associated with different types of cancer, even though the tumor and its metastases have not invaded the nervous system (1, 2, 3, 4 5, 6, 7, 8, and 9). These "remote effects" of cancer, or paraneoplastic syndromes, are of undetermined etiology, although some studies have implicated viral, hormonal or toxic origins (1, 6, 10, and 11). Alternatively, others have thought that these degenerative diseases may stem from an autoimmune response which is directed towards antigens or epitopes found in both the tumor and specific neurons (12, 13, and 14). Evidence supporting this connection has been presented in the case of Eaton-Lambert myasthenic syndrome, a disease of the peripheral nervous system, in which the binding of autoantibodies at the neuromuscular junction interferes with the calcium-induced release of neurotransmitter (15, 16, and 17). An autoimmune component also has been suggested in several diseases of the central nervous system, including paraneoplastic cerebellar degeneration (12, 18, and 19) and cancer-associated retinopathy (20, 21, 13, 14, 22, and 23).

With cancer-associated retinopathy ("CAR") retinal degeneration often precedes diagnosis of the tumor, and loss of vision may occur rapidly. Like other retinal degenerations, CAR spares the inner retina while causing photoreceptors to degenerate (20 and 13). However, during CAR there is no evidence of pigment migration or epiretinal membrane formation, as occurs in retinitis pigmentosa, nor are the vasculature or optic nerve head damaged (20). The inflammatory response characteristic of uveitis is not associated with CAR. Despite these differences, autoantibodies may be involved in all of these degenerative diseases of the retina (24). Retinal antigens of 58–62 kDa, 145 kDa and 205 kDa have been observed to bind antisera obtained from patients with retinitis pigmentosa and age-related macular degeneration (25 and 26). An earlier study of CAR also identified a retinal antigen of 65 kDa, as well as a low molecular weight protein of approximately 20 kDa (21). More recent and extensive studies of CAR have focused on a prominent retinal antigen of approximately 23 kDa (12, 22, and 23). Several of these antisera cross-react with the 68 kDa neurofilament protein, and this finding has led to the speculation that autoantibodies associated with retinal degenerations may be directed towards cytoskeletal elements found in the tumor and retinal cells (21 and 26).

The results obtained from immunohistochemical studies using CAR antisera have been inconsistent; different populations of retinal cells have been labeled by different CAR antisera (13, 14, and 22). However, antibodies from these complex human sera were not affinity-purified, therefore, it was difficult to associate a specific antibody with a particular labeling pattern. Nor were EM-immunocytochemical studies performed. For these reasons, the identity of the retinal antigen that binds the CAR autoantibodies and its precise localization remained uncertain. The functional identification of the CAR antigen also had not been ascertained.

Presently, there is no laboratory test which can conclusively diagnose CAR. A positive test for the presence of CAR autoantibodies would aid in the diagnosis of the retinal disease and enable the physician to treat effectively the patient and prevent or delay further vision loss. Moreover, since the neurological symptoms often occur prior to the diagnosis of cancer, a positive antibody response may act as an early warning for cancer in these patients.

Therefore, a general object of the present invention is to provide a laboratory method and diagnostic test for diagnosing cancer-associated retinopathy.

Another object of the invention is to provide a novel method which utilizes a purified cancer-associated retinopathy autoantigen in a patient-serum assay to detect the presence of cancer-associated retinopathy autoantibodies.

Still another object is to provide a method for identifying and purifying a cancer-associated retinopathy autoantigen.

Given the above background, the present invention proposes a novel method for diagnosing cancer-associated retinopathy employing the fundamental steps of acquiring a purified aliquot of 26 kDa protein, and, utilizing selectively either the protein or peptides derived therefrom, performing a patient-serum assay to identify in a sample of a patient's serum the presence of autoantibodies to 26 kDa protein autoantigen. Acquisition of such an aliquot can occur, for example, through a purification procedure proposed herein as a feature of this invention, through production (via synthesizing) of protein fragments, or through a production of recombinant 26 kDa protein.

In accordance with one way of viewing a preferred method of practicing the invention, such practice includes the steps of identifying as a cancer-associated retinopathy herald a 26 kDa protein autoantigen, acquiring from a selected retina source and purifying from the source an aliquot of 26 kDa protein, and performing a patient-serum assay utilizing such 26 kDa protein to identify autoantibodies in the patient's serum to the 26 kDa protein.

These and other objects and features of the present invention will become more fully apparent when the following detailed description of a preferred embodiment is read in connection with the accompanying drawings.

DETAILED DESCRIPTION AND BEST MODE FOR CARRYING OUT THE INVENTION

Using the sera from five individuals, applicants have identified a 26 kDa CAR autoantigen that is localized with highest density to the cell bodies of the retinal rods and cones but also is found in the inner and outer segments of both types of photoreceptors. Further, applicants have purified the 26 kDa CAR autoantigen to homogeneity using a convenient, two-step chromatographic procedure. Cleavage products of the purified protein were used to determine the amino acid sequence of the protein, which was identified as a member of a family of calcium binding proteins. Using either the purified (derived) protein, or synthetic peptides derived from the known sequence of the protein, applicants can test the serum from patients suspected of having CAR and related diseases for the presence of autoantibodies.

In order to identify and, then, to purify the autoantigen associated with cancer-associated retinopathy, it is first necessary to affinity-purify autoantibodies present in CAR antisera. Therefore, in this detailed description, applicants will initially describe the affinity-purification of antibodies from CAR antisera, and the use of these antibodies in parallel Western blot analyses and EM-immunocytochemical studies.

Preparation of Human Rod Outer Segments

Rod outer segments (ROS) were isolated from human retinas according to the procedures developed for bovine ROS, as described by Papermaster (27). In other experiments, human retinas were disrupted using a Teflon pestle and solubilized with 0.15% wt/vol deoxycholate. After centrifugation at 100,000 g (SW28; Beckman Instruments, Fullerton, Calif.), the supernatant and previously isolated ROS were processed for SDS-PAGE. All isolations were done in the presence of protease inhibitors: 2 µg/ml leupeptin, 4 µg/ml PMSF, and 10 µg/ml aprotinin.

SDS-PAGE and Western Blot Analysis

Treatment of protein samples is described in detail elsewhere (28), as are the procedures for electrophoresis and transfer of protein to nitrocellulose (29). In some experiments, Immobilon™ (Millipore Corp., Bedford, Mass.) was used in place of nitrocellulose. Separation of peptide fragments was accomplished with a Tricine-SDS-gel electrophoresis system (30 and 31) using a 16% polyacrylamide gel. Protein determinations were made with a dye binding assay (32).

Western blots were rinsed twice in Tris·NaCl, and non-specific sites were saturated by incubation for 45 minutes at 37° C. with a solution of Tris·NaCl containing 5% wt/vol BSA. The membrane then was incubated for 1–2 hours either with CAR antisera at a dilution of 1:500 or affinity-purified antibody (see below). All incubations were performed in 0.1% BSA-Tris·NaCl. Blots were rinsed six times each for 5 minutes with 0.1% BSA-Tris·NaCl and then incubated for 2 hours with a 1:50 dilution of goat anti-human IgG gold conjugate in 0.1% BSA-Tris·NaCl containing 0.4% wt/vol gelatin. After four rinses with 0.1% BSA-Tris·NaCl, blots were rinsed with water (twice for 30 seconds each) and silver-enhanced 10–15 minutes according to the manufacturer's procedures.

Affinity-Purification of CAR Antibodies

Procedures for the affinity-purification of complex antisera have been published in detail elsewhere (33). Briefly, blots of human ROS protein were incubated with CAR antiserum. A single lane from the blot was stained using gold conjugates and silver enhancement as described above. The stained lane was realigned with the blot, and protein bands corresponding to the sites of antibody staining were excised separately. Antibody was eluted from excised bands using glycine·HCl, pH 2.2, followed by neutralization with Tris base. The antibody eluate was quantitated for human IgG using an immunogold procedure (33). After concentrating the eluate in a Centricon 30 tube (Amicon Corp., Danvers, Mass.), the sample was mixed with a further solution to yield 0.1% BSA, 0.1% normal goat serum in either Tris·NaCl or PBS. In this manner, we have demonstrated that only autobodies to 26 kDa protein found in retina correlated with CAR (41).

Purification of the 26 kDa CAR Antigen

ROS from 150 bovine retinas was prepared as described previously (34) and finally resuspended in 20 ml of 50 mM Hepes buffer, pH 7.5, containing 1.0 mM EDTA and 100 mM NaCl. The suspension was homogenized with a glass-glass tissue homogenizer and centrifuged at 48,000 g (J 20.1; Beckman Instruments) for 10 minutes. The supernatant was collected and the extraction procedure was repeated three times. These steps were conducted at 4° C. under dim red illumination. Calcium chloride then was added to the combined supernatants in order to yield a final concentration of 2 mM.

A Phenyl-Sepharose column (1.0×4.0 cm) was prepared and equilibrated with 50 mM Hepes buffer, pH 7.5 containing 2 mM $CaCl_2$ and 100 mM NaCl. The bovine ROS extract was applied to the column and the column was washed with equilibrating buffer at a rate of 15 ml/h until the $A_{280}$ nm returned to the baseline. Bound material was eluted with 50 mM Hepes buffer, pH 7.5, containing 10 mM EDTA and 100 mM NaCl at a rate of 5 ml/h. One ml fractions were collected, and aliquots were subjected to SDS-PAGE and Western blot analysis using CAR antiserum.

Fractions containing the 26 kDa CAR antigen were combined and dialyzed against 1 liter of 10 mM bis [2-hydroxymethyl] iminotris [hydroxymethyl]-methane (BTP) buffer, pH 8.4. Aliquots containing 0.5–1.0 mg of protein were applied to a Mono Q column polystyrene divinylbenzene resin (HR 5×50 mm; Pharmacia Fine Chemicals, Piscataway, N.J.) equilibrated with 10 mM BTP buffer, pH 8.4. The column was developed with a linear gradient of NaCl (0–0.25M) during 20 minutes at a rate of 0.5 ml/min. 0.5 ml fractions were collected, and aliquots were analyzed by SDS-PAGE and Western blot analysis using CAR antiserum. The 26 kDa CAR antigen eluted at ~100 mM NaCl.

Figure 1:
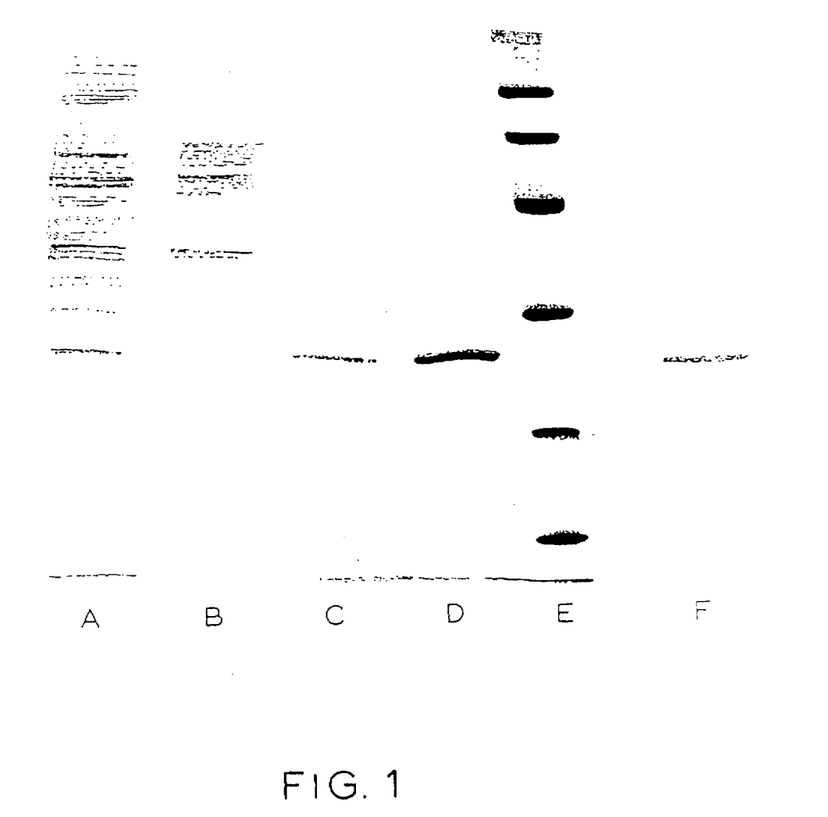
FIG. 1 shows the SDS-PAGE electrophoresis staining pattern of purified CAR antigen.

As seen in FIG. 1, bovine rod outer segments were extracted with EDTA, and the soluble fraction (after adjusting the calcium concentration) was applied to a Phenyl-Sepharose column. An aliquot of the soluble extract was separated by SDS-PAGE, and the protein staining pattern is shown in lane A. Protein which did not bind to the column is shown in lane B, whereas bound material which could be eluted with EDTA is stained in lane C. The 26 kDa CAR protein represented the majority of protein which was bound to the column. The eluted material depicted in lane C was further purified by Mono Q chromatography, and an aliquot of the final sample is shown in lane D. Molecular weight standards in lane E were: phosphorylase b (94 kDa), bovine serum albumin (67 kDa), ovalbumin (43 kDa), carbonic anhydrase (30 kDa), soybean trypsin inhibitor (20 kDa), and alpha-lactalbumin (14 kDa). An immunoblot of the purified fraction shown in lane D was prepared according to the procedures essentially described by Towbin et al., 1979. CAR staining of the immunoblot is shown in lane F demonstrating that the purified 26 kDa protein is the immunoreactive antigen recognized by CAR antisera.

The purified protein can be used as a substrate for ELISA (as described below), or synthetic peptides derived from the known sequence of the 26 kDa protein (see FIG. 2 (SEQ ID NO:1)) can serve as substrate in the assay.

Amino Acid Sequence Analysis

The purified 26 kDa CAR protein was lyophilized and S-carboxymethylation was performed following the methods described by Crestfield et al. (35). Cyanogen bromide (CNBr) cleavage of the S-carboxymethylated protein was performed over a 72-hour period according to the methods published by Lai (36). CNBr peptide fragments were separated by Tricine-SDS-gel electrophoresis (30 and 31) and electroblotted to Immobilon (Millipore Corp.) for sequence and amino acid analysis (37). Additionally, the purified 26 kDa protein was subjected to cleavage at lysyl residues with endoproteinase Lys-C (Boehringer-Mannheim Biochemicals, Indianapolis, Ind.), and peptides were isolated by narrowbone RP-HPLC (Vydac, Hesperia, Calif.) using, the Applied Biosystems model 130 system (Applied Biosystems, Inc., Foster City, Calif.) (38).

Phenylthiocarbamyl amino acid analysis was performed according to West and Crabb (39) using an Applied Biosystems automatic system (models 420/130/920). HCl vapor phase hydrolysis was performed at 150° C. for 1 hour.

Automatic Edman degradations were performed as previously described (40) with an Applied Biosystems gas phase sequencer (model 470) and an on-line phenylthiohydantoin amino acid analyzer (model 120) using the 03RPTH sequencer program and the manufacturer's recommended program and solvents for the PTH analyzer.

Figure 2:
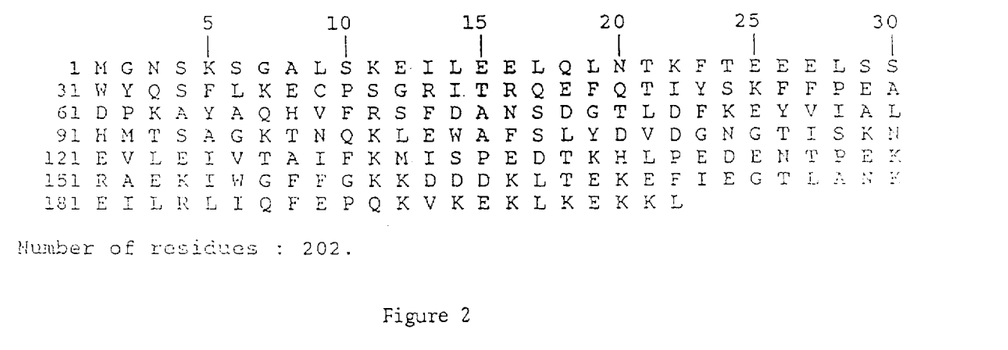
FIG. 2 shows the amino acid sequence of the 26 kDa CAR antigen (SEQ ID NO:1). The single letter code for amino acids is used (Eur. J. Biochem. 1968, 5:151–153).

FIG. 2 illustrates the known sequence of the purified 26 kDa protein/CAR autoantigen (SEQ ID NO:1). The single letter code for amino acids is used (Eur. J. Biochem, 1968, 5:151–153).

EXAMPLE 1

Enzyme Linked Immunosorbent Assay

Purified 26 kDa protein is adsorbed to polystyrene 96-well microtiter plates (Corning Glass Works, Corny, N.Y.) by incubation overnight in Tris buffer, pH 9.0. Additional vacant sites on the plates are blocked by incubation with 1% w/v BSA for 1 hr. at room temperature. After washing the plates with 0.1% w/v BSA, serum obtained from patients is serially diluted from 1/100 to 1/2,500 and a total volume of 100 µl is added to the wells. A second set of wells is incubated with normal human serum which serves as a control. Incubation is conducted at room temperature for 1 hour. After thorough washing, 100 µl of a commercially-available secondary antibody (goat anti-human IgG) conjugated with horseradish peroxidase (Vector Laboratories, Burlingame, Calif.) is added to the wells at 1 µg/ml, for a 30-min. incubation. Alternatively, for greater sensitivity, the detection system can consist of incubations with 100 µl of a 1 µg/ml solution of biotinyl goat anti-human IgG (Vector Laboratories) followed by streptavidin-horseradish peroxidase complex (Amersham Corp., Arlington Heights, Ill.) at the same concentration. (Other enzyme-linked secondary antibodies, i.e., alkaline phosphatase, also can be used for detection.) The commercially-available substrate,3,3',5,5'-tetramethylbenzidine (TMB) (Biorad Laboratories, Richmond, Calif.), in the presence of hydrogen peroxide, is then added according to the manufacturer's directions, to visualize antibody binding. The reaction can be visually inspected or quantified using a plate reader. The patient's serum is compared to the control consisting of normal human serum.

Alternatively, synthetic peptides derived from the 26 kDa protein can be conjugated to a carrier molecule, i.e., BSA, and adsorbed to microtiter wells for the enzyme-linked immunosorbent assay ("ELISA"), as just described.

Figure 3A:
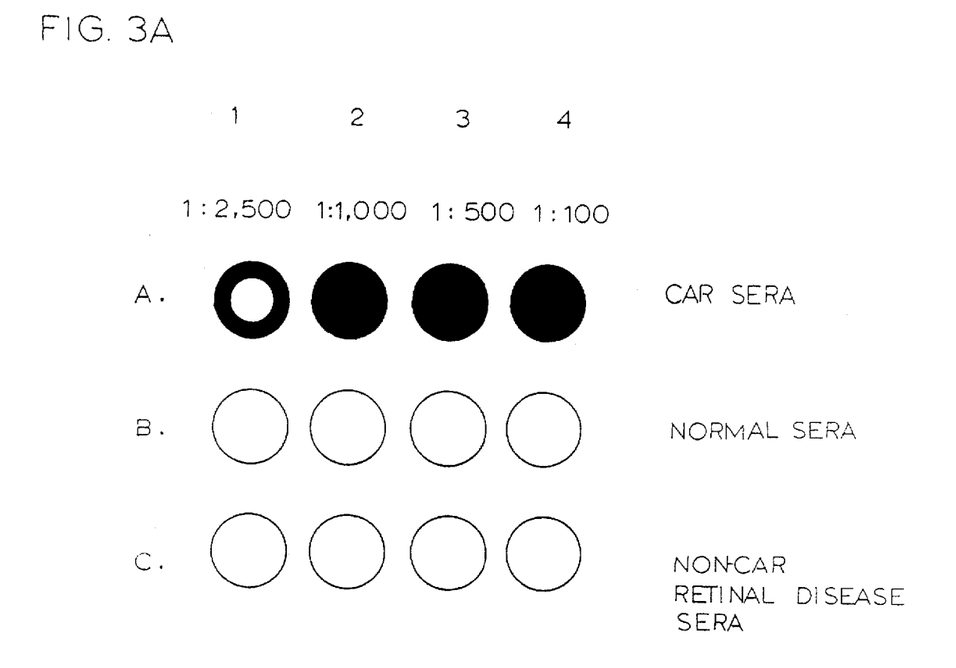
FIG. 3A illustrates, in rows A, B and C for each of three different patients—CAR patient, NORMAL patient and NON-CAR RETINOPATHY patient, respectively—the visually observable binding reactions of respective dilution series for the three patients.
Figure 3B:
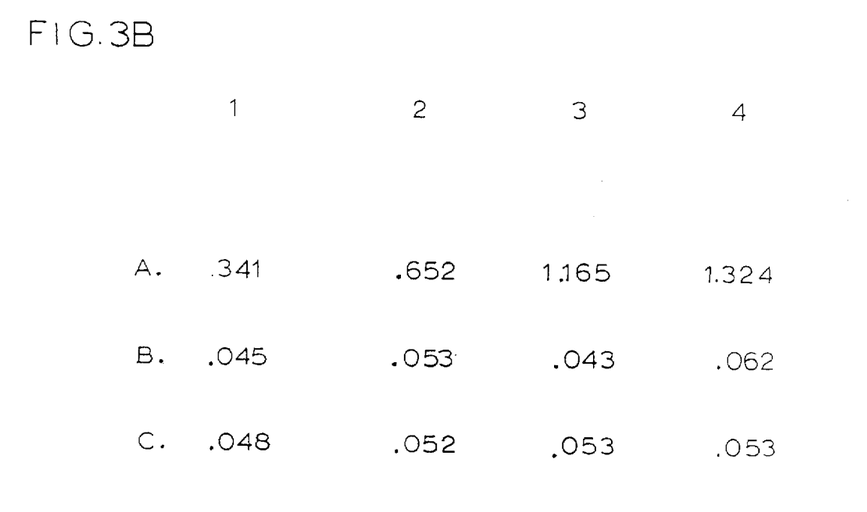
FIG. 3B, in rows A, B and C, presents quantified spectrophotometric data associated with the reactions pictured in FIG. 3A.

FIG. 3A illustrates the binding of a CAR serum sample to wells of a microtiter plate that have been coated with purified 26 kDa protein. The microtiter plate can be visually inspected for dark reaction product indicative of a positive binding response, as in FIG. 3A, or such antibody binding can be quantified spectrophotometrically using a microtiter plate reader (Biorad Laboratories) as shown in FIG. 3B. FIGS. 3A and 3B illustrate two controls. Both normal human serum and the serum from a patient with a retinal disorder other than CAR do not bind to the microtiter wells coated with the 26 kDa CAR protein. Thus, antibody binding correlates precisely with CAR. (As demonstrated in our publication, Polans et al., 1991, patients with retinal degenerations other than CAR do not display autoantibodies to the 26 kDA protein. Patients with similar cancers as the CAR patients but who do not have an associated retinopathy also do not have autoantibodies to the 26 kDa protein. Finally, individuals with other autoimmune disorders, such as Guillain Barre and Lupus, also do not have autoantibodies to the 26 kDa protein.)

EXAMPLE 2

Western Blot Analysis

In addition to the recoverin ELISA described in example 1, the presence of recoverin autoantibodies in the sera of suspected CAR patients can be determined by Western blot analysis. This procedure has the added advantage of displaying the molecular weight of the reactive protein (recoverin), thus providing further certainty about the specificity of the antibody/recoverin reaction.

Recoverin, the CAR autoantigen, is isolated from human or bovine retinas by a combination of phenyl-Sepharose chromatography and Mono Q chromatography as described previously (41 and 42).

Purified recoverin is resolved on a 0.75 mm, 15% polyacrylamide gel and electrotransferred to Immobilon (Millipore Corp., Danvers, Mass.). The Immobilon blots are rinsed twice in 20 mM Tris-HCl, 0.9% NaCl, pH 8.2, and nonspecific sites are saturated by incubation for 45 min. at 37° C. with a solution of 5% w/v bovine serum albumin (BSA) in 10 mM Tris-HCl, 0.9% NaCl, 0.05% v/v Tween-20, pH 8.0 (TBST). Blots are incubated with the patient's serum for 1 hr. in TBST that contains 1% w/v BSA and 1% v/v normal goat serum. After 3×10 min. washes with TBST, blots are incubated for 30 min. with an alkaline phosphatase conjugated goat anti-human IgG (commercially available from many vendors) at a dilution of 1:5,000 using TBST that contains BSA and normal goat serum. After washing with TBST, antibody binding is detected using BCIP and nitro blue tetrazolium (NBT) as substrates according to the manufacturer's recommended procedures (Promega, Madison, Wis.). A blue band corresponding to the molecular weight of recoverin (23–26 kDa) will appear if the patient's serum contains autoantibodies to recoverin (the CAR antigen), and this finding will confirm the diagnosis of cancer associated retinopathy (CAR). Other detection systems are commercially available for staining Western blots as alternatives to the alkaline phosphatase conjugated anti-human IgG, and will provide the same information.

In summary, applicants have affinity-purified the autoantibodies from complex CAR sera to identify the principal, if not sole, retinal antigen as a 26 kDa protein. In EM immunocytochemical experiments, applicants localized the 26 kDa protein to the cell bodies, inner and outer segments of both rods and cones. Applicants purified the rod protein by a two-step chromatographic procedure and developed a laboratory method and diagnostic test for identifying the presence of CAR autoantibodies in a patient's serum by using applicants' purified autoantigen.

Owing to the characterization of the 26 kDa protein, it is also now possible to examine biopsy tissue obtained from CAR patients and look for the expression of an immunoreactive calcium-binding protein or shared determinant.

While a preferred embodiment of the invention has been described, it should be appreciated that variations and modifications may be made without departing from the scope of the invention as defined by the claims.

It is desired to claim and secure by Letters Patent:

1. An isolated protein of about 26 kDA or a peptide derived therefrom which is specifically bound by purified CAR antibodies wherein the protein has an amino acid sequence as shown in SEQ ID NO: 1.

2. The protein of claim 1 wherein the isolated protein exhibits an SDS-PAGE electrophoresis profile as shown in lane D of FIG. 1.

3. An isolated protein comprising an amino acid sequence as shown in SEQ ID NO: 1 or a peptide derived therefrom which is specifically bound by purified CAR antibodies.

4. The protein of claim 3 wherein said amino acid sequence or peptide derived therefrom is conjugated to a carrier molecule.

5. The protein of claim 4 wherein the carrier molecule is bovine serum albumin.

6. The protein of claim 3 wherein said amino acid sequence or peptide derived therefrom is adsorbed to a solid support.

7. The protein of claim 6 wherein the solid support is a microtiter plate.

8. The protein of claim 6 wherein the solid support is polystyrene.

9. The protein of claim 3 wherein said amino acid sequence or peptide derived therefrom is immobilized on a polyvinylidene fluoride membrane.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 202 amino acids
        ( B ) TYPE: amino acid
        ( D ) TOPOLOGY: linear     ( i i ) MOLECULE TYPE: protein     ( i i i ) HYPOTHETICAL: NO     ( i v ) ANTI-SENSE: NO     ( x i ) SEQUENCE DESCRIPTION: SEQ ID NO:1:

```
Met Gly Asn Ser Lys Ser Gly Ala Leu Ser Lys Glu Ile Leu Glu Glu
  1               5                  10                  15

Leu Gln Leu Asn Thr Lys Phe Thr Glu Glu Glu Leu Ser Ser Trp Tyr
             20                  25                  30

Gln Ser Phe Leu Lys Glu Cys Pro Ser Gly Arg Ile Thr Arg Gln Glu
         35                  40                  45

Phe Gln Thr Ile Tyr Ser Lys Phe Phe Pro Glu Ala Asp Pro Lys Ala
     50                  55                  60

Tyr Ala Gln His Val Phe Arg Ser Phe Asp Ala Asn Ser Asp Gly Thr
 65                  70                  75                  80

Leu Asp Phe Lys Glu Tyr Val Ile Ala Leu His Met Thr Ser Ala Gly
                 85                  90                  95

Lys Thr Asn Gln Lys Leu Glu Trp Ala Phe Ser Leu Tyr Asp Val Asp
```

```
                    100                    105                         110
    Gly Asn Gly Thr Ile Ser Lys Asn Glu Val Leu Glu Ile Val Thr Ala
            115             120                 125
    Ile Phe Lys Met Ile Ser Pro Glu Asp Thr Lys His Leu Pro Glu Asp
        130             135                 140
    Glu Asn Thr Pro Glu Lys Arg Ala Glu Lys Ile Trp Gly Phe Phe Gly
    145             150                 155                         160
    Lys Lys Asp Asp Asp Lys Leu Thr Glu Lys Glu Phe Ile Glu Gly Thr
                    165                 170                     175
    Leu Ala Asn Lys Glu Ile Leu Arg Leu Ile Gln Phe Glu Pro Gln Lys
                180                 185                     190
    Val Lys Glu Lys Leu Lys Glu Lys Lys Leu
            195                 200
```